United States Patent [19]

Thrun

[11] 4,243,140
[45] Jan. 6, 1981

[54] SURGICAL NEEDLE AND SHARPS HOLDING CONTAINER

[75] Inventor: Robert H. Thrun, Lisle, Ill.

[73] Assignee: Anchor Products Company, Addison, Ill.

[21] Appl. No.: 57,290

[22] Filed: Jul. 13, 1979

[51] Int. Cl.³ ............................................. A61L 17/02
[52] U.S. Cl. ................................. 206/380; 206/382; 206/459; 206/460; 206/523; 229/2.5 R; 220/339
[58] Field of Search ............... 206/380, 382, 63.3, 206/45.34, 523, 813, 459, 460; 229/2.5 R; 220/339

[56] References Cited
U.S. PATENT DOCUMENTS

| 1,724,208 | 11/1955 | Nelson | 206/45.34 |
| 4,008,802 | 2/1977 | Freitag | 206/382 |
| 4,167,230 | 9/1979 | Barrett | 206/380 |
| 4,193,496 | 3/1980 | Barrett | 206/382 |

Primary Examiner—William T. Dixson, Jr.
Attorney, Agent, or Firm—McDougall, Hersh & Scott

[57] ABSTRACT

A hinged disposable container for retaining surgical implements is disclosed. The container is provided with one or more elongated strips of a resilient material. The surgical implements are retained by inserting them into slots formed in the strip, and numerical indications enable the user to precisely determine the number of needles in the container. Separate adhesive means are provided for holding other sharps in position.

6 Claims, 7 Drawing Figures

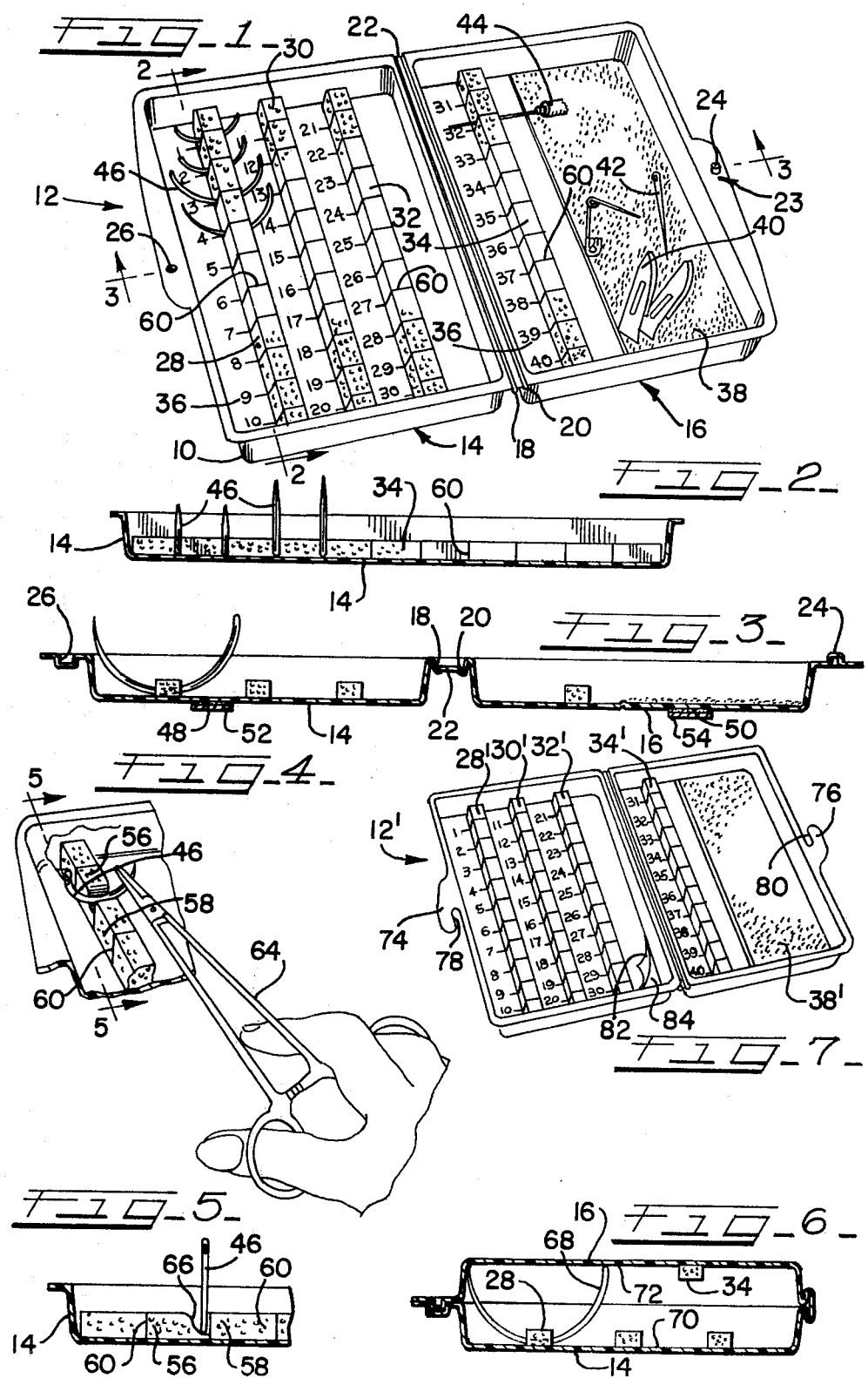

SURGICAL NEEDLE AND SHARPS HOLDING CONTAINER

BACKGROUND OF THE INVENTION

The present invention relates to containers for receiving surgical needles and other small surgical implements. More specifically, it relates to containers which are used to receive these surgical implements during an operation and which provide a systematic means for counting the implements after use and/or as they are removed from the body of the patient. Furthermore, the containers provide a means for disposing of the sharp instruments after the operation is completed.

Surgical practice has long recognized the danger of the possibility that small surgical implements may be left within the body of a patient during surgical procedures. Even the most acute visual inspection of the patient will often not reveal the presence of surgical implements which are left within the patient's body. However, to assure that all the implements are removed, an accounting system is often used. The number of implements available to the surgeon are counted before the operation and again counted as they are removed from the patient's body. In this way, the lack of an implement at the end of the operation indicates that it has been misplaced and possibly inadvertently left within the patient's body, and a visual search of the area including the incision can be performed until the implement is found.

Although the implements may be routinely counted before the operation, during the closure of the incision the count must be made with great rapidity so as to not extend the amount of time that the patient is under surgery. This process of counting the implements can be facilitated by devices which are used to retain the blades, surgical needles, staples, and other small implements as they are used and/or removed from the patient as the case may be. These are disclosed in U.S. Pat. No. 3,944,069 to Eldridge; U.S. Pat. No. 4,013,109 to Sandel; and U.S. Pat. No. 4,008,802 to Freitag.

U.S. Pat. No. 3,944,069 to Eldridge discloses a "Receiver for Disposable Surgical Implements" which is provided with a pair of foldably connected pads which each have a penetrable top layer and a penetration-resisting bottom lamination. As each surgical implement is removed from the patient, it is inserted through the top layer and retained for eventual counting. The pads may then be folded together covering the sharp edges and then safely disposed of. U.S. Pat. No. 4,013,109 to Sandel discloses a hinged container for magnetizable surgical needles. As the instruments are removed from the body, they are deposited within the container and held in position there by a magnetic means which completely covers the interior portion of the case. Following surgery, the container may be folded and the instruments safely disposed of. Finally, U.S. Pat. No. 4,008,802 to Freitag discloses a pad of resilient material which is provided with consecutively numbered receiving zones. The needles are inserted through ridges which are upstanding from the upper face of the pad. After the instruments have been accounted for, the pad may be folded and disposed of.

These devices in the prior art are not without some significant shortcomings.

Eldridge discloses the receiver which utilizes a top lamination through which the sharp instruments may be inserted. As the surgery progresses, various implements such as hypodermic needles, surgical needles, and small surgical knives can be inserted through whatever portion of the lamination is not already occupied by previously removed implements. However, since the instruments are apt to be inserted through the lamination in a random position and orientation, the task of accounting for them is not greatly facilitated by this device.

U.S. Pat. No. 4,008,802 to Frietag discloses a Surgical Needle Retaining and Inventory Pad and Accounting Method, and utilizes parallel ridges upstanding from the face of the pad with the pad being delineated into a series of zones. The portion of the ridges in each zone is consecutively numbered. As the needles are removed from the body, they are inserted through the ridge in each needle-retaining zone. However, since the needle or other object can only be attached to the ridge by puncturing the material and pushing the instrument through, the instrument itself must be pointed or sharp and also must be held in a proper orientation and manner to accomplish this puncturing operation.

Another device known in the prior art utilizes the physical principle of the attraction between ferrous metals and magnetized surfaces. Such devices are disclosed in U.S. Pat. No. 3,727,658 to Eldridge, and U.S. Pat. No. 4,013,109 to Sandel. Two critical shortcomings of these devices are the facts that only ferrous materials can be retained by the magnetic surfaces and there is a tendency for the ferrous materials to become magnetized themselves and thus be attracted to each other.

A further shortcoming of containers known to the inventor is that although the packages equipped with means to retain the surgical instruments may be marked into consecutively numbered zones, they can sometimes cause confusion in the accounting of the instruments. For example, if a magnetic surface were to be delineated into zones, implements could be placed close to the border between adjacent zones and create confusion in accounting for the instruments. It may appear that a zone is occupied when it actually is not. Alternately, a large instrument may be inadvertently placed straddling the division between two zones and thus may create the appearance that two smaller instruments are placed in the two zones. Of course, such problems can also be present when the instruments are retained by puncturing the laminar or ridged surface since the insertion may take place in one zone and the point protrude from another. This shortcoming is more than just an inconvenience to the surgeon or scrub nurse who counts the implements. It can cause unnecessary delays in the closure of the incision or may cause complications if it leads to an implement being left inside the body of the patient.

Hence, it is an object of this invention to provide a receiver for surgical instruments which facilitates the orderly arrangement of implements as they are removed from the body.

It is another object of this invention to provide a surgical needle container which may retain surgical instruments without the instruments having to pierce the surface by which they are to be retained.

An additional object of the present invention is to provide a container for surgical instruments which can retain both ferrous and nonferrous instruments and not affect their magnetic characteristics.

It is another object of this invention to provide a container for surgical needles which will facilitate the placement of a single instrument in a single receiving zone.

Other objects and advantages of the invention will become apparent from the remaining portions of the specification.

BRIEF SUMMARY OF THE INVENTION

The foregoing and other objects of the invention are achieved by providing a container for surgical instruments with one or more elongated strips of resilient material into which regularly spaced narrow slots extending perpendicular to the strips' length are formed. Surgical instruments are inserted into these slots and are functionally retained there by the resiliency of the strips. An indicia of sequential numbers are provided adjacent to each slot to facilitate the counting of the instruments.

BRIEF DESCRIPTION OF THE DRAWINGS

The invention itself is set forth in the claims appended hereto and forming a part of this specification while an understanding of the embodiment thereof may be had by reference to a detailed description taken in conjunction with the drawings in which:

FIG. 1 is a perspective view of the preferred embodiment of the invention;

FIG. 2 is a cross-sectional view along line 2—2 of FIG. 1;

FIG. 3 is a cross-sectional view along line 3—3 of FIG. 1;

FIG. 4 is a perspective view of a needle being inserted into a retaining slot of the container;

FIG. 5 is a cross-sectional view along line 5—5 of FIG. 4;

FIG. 6 is a cross-sectional view along line 3—3 showing the container in a closed position; and, FIG. 7 is a perspective view of another embodiment of the invention with an alternative fastening means.

DETAILED DESCRIPTION OF THE INVENTION

Referring to FIG. 1, the preferred embodiment of the invention is illustrated. The outside shell 10 of the container 12 is comprised of two open-topped boxes 14 and 16 which are provided with live hinges 18 and 20 as well as spacer 22. The shell, hinges, and spacer are vacuum molded from a rigid plastic material such as polystyrene. A closure lock 23 having a male section 24 and a female section 26 is also provided.

Each compartment of the preferred embodiment is provided with one or more elongated strips which are to retain the surgical implements. In the container illustrated the left compartment is provided with three elongated strips 28, 30 and 32 while the right compartment is provided with a single strip 34. Each strip is provided with narrow slots at ten regularly spaced intervals. Thus the container illustrated can retain up to 40 implements at the slotted strips. Adjacent to every strip is an arrangement of consecutive numbers 36 which correspond to each slot. In this embodiment the indicia is molded into the shell itself. In alternate embodiments the indicia may be printed directly upon the surface or may be printed on a paper backing which can be attached to the shell wall adjacent to the elongated strips by use of adhesives, staples, or other suitable means.

In addition to the elongated strip 34, the right compartment is provided with a surface 38 which is coated with an adhesive film. Objects which are unsuitable for retention in the slots may be deposited on the surface and be retained there by the adhesive film. For example, the illustrations shows blades 40 and pins 42 retained on the adhesive surface while hypodermic needle 44 and suture needle 46 are retained in the slots of the elongated strips.

The container is also provided with strips 48 and 50 of pressure-sensitive tape which are normally covered with masking strips 52 and 54. When the container is to be used in the operating room, the masking strips are removed and the container may be attached to the surface of a back table. This use of the adhesive strips will prevent the container from sliding along the horizontal surface it rests on during the operation. Of course, any accidental overturning of the container would also be prevented.

FIGS. 2 and 3 illustrate a cross-sectional view of the slotted strips with curved suture needles retained in the slotted strips. The strip is constructed of a resilient material such as closed-cell polyurethane foam, or other resilient artificial or natural compounds. When a needle or other implement is inserted into a slot, the resilient surfaces at either side of the slot are slightly deformed and retain the implement in the slot by frictional forces.

FIGS. 4 and 5 show a sectional illustration of the slotted strips showing the self-seating feature of the strips. This action allows the easy insertion of the implements in the slots. The strip 28 is divided by slot 60 into a number of subsections. In the illustration, the second slot 60 divided subsections 56 and 58. A surgeon holding the suture needle 46 by means of forceps 64 can use the needle to compress any portion of the subsection 56. Although the slot is not exceptionally visible when the strip is not compressed, it does become apparent when the subsection to either side of it is compressed. Not only does the slot become visible, but the subsection 56 forms a declined surface 66 which is sloped toward the nearest slot 60. The combination of the declined surface and the pressure exerted by the surgeon will urge the needle into the slot.

Another technique for inserting the needle into the slot is simply to dispose the needle against the top surface of a subsection and move it toward the position of the slot. Of course, when the needle reaches the proximity of the slot, the subsection will deform sufficiently for the needle to be urged into the slot.

FIG. 4 also illustrates how the suture needle can be held by either its pointed end, as illustrated, or, of course, by the end which is threaded. Since the needles need not puncture the surface of the strip, the surgeon or scrub nurse does not have to be concerned with which end of the suture needle is held by the forceps before the needle is inserted into the container. This obviates delays in the surgery which could be caused if the needles would have to be inserted through the surface of the strips since in that event it would often be necessary to reposition the needle in the forceps.

The container illustrated is provided with indicia of consecutive numbers which are adjacent to the series of slots in the elongated strips. It should be noted that there are ten slots provided in each strip. The use of a series of ten slots facilitates the counting of the implements since the surgeon or scrub nurse can more easily tally the amount of implements by multiples of ten. For example, two filled strips indicates 20 implements, or three filled strips indicates 30 implements are retained. This, of course, is a much easier tallying system than if, for example, seven slots were provided and the filled strips represented the retention of implements in multiples of seven.

It is common surgical practice to dispose of the small surgical implements following the operation rather than sterilizing them for reuse. Great care must be exercised in the disposal of the implements because of their dangerously sharp edges and points. The invention herein disclosed facilitates the safe disposal of the implements in that it securely retains them and also encloses the sharp edges and points which reduces the risk of infection for the operating room staff. When the operation is completed and the implements counted, the medical personnel can fold the container together by means of the live hinges 18 and 20 and spacer 22. As can best be seen in FIG. 6, the two sections of the container form a closed box which is fastened shut by the closure lock 23 due to the action of the male and female sections 24 and 26.

It should be noted that the container should be dimensioned so that the distance between the opposite surfaces is larger than a dangerous axis of an implement. For example, the suture needle 68 shown in FIG. 6 may assume an orientation so that when closed, its point could be forced through the wall of the container. However, since the distance separating wall 70 and 72 is greater than the dangerous curved axis of the needle, the possibility of penetrating wall 70 is greatly reduced.

FIG. 7 shows an alternate embodiment 12' of the invention where another design of closure lock is used. Instead of molding the container to provide male and female sections, a hooked member is provided on each side. Specifically, hooked tabs 74 and 76 define slots 78 and 80, respectively.

The tabs 74 and 76 are of thin plastic and when the container is folded for disposal, the tabs are readily bent and hooked together to securely attach the two sections of the container. It will be appreciated that other common fastening techniques could also be employed, for example, a hook and loop closure sold under the trademark "Velcro".

FIG. 7 also illustrates the aforementioned alternative wherein a pressure-sensitive adhesive paper 82, or the like (shown partially stripped back) is disposed on wall 84 to provide the indicia 36'. Paper on the other wall 86 may also display instructions or other information, or this material may be molded into the wall. The strips 28'–34' and adhesive 38' are, of course, fixed in place on top of the paper.

It will be understood that various changes and modifications could be made in the embodiments of the invention disclosed without departing from the spirit of the invention particularly as defined by the following claims.

I claim:

1. In a hinged disposable container for retaining surgical implements, the improvement comprising: an outside shell means for completely containing the implements comprised of two open-topped boxes; a hinge means for pivotally attaching said open-topped boxes to each other so that said open-topped boxes may be disposed against each other to form one continuous enclosure; a closure means to maintain said open-topped boxes in a closed position; an elongated resilient strip of resilient material which is provided with one or more slots, each slot defining resilient surfaces on either side of the slot which make contiguous contact and are slightly deformed upon a surgical implement being inserted into the slot so as to retain the implement by the frictional forces exerted by said surfaces, said strip being attached to an inside surface of at least one open-topped box; and numerical indicia means provided adjacent to said slots so that each slot is indicated with a sequential number.

2. In the hinged disposable container of claim 1, the improvement further comprising the provision of an adhesive film means at the interior of at least one of the open-topped boxes so that surgical implements may be retained within said box by disposing them against said adhesive film.

3. In the hinged disposable container of claim 1, the improvement further comprising the provision of said indicia printed upon a paper backing and said paper backing being attached to said container so that said indicia is adjacent to each slot.

4. In the hinged disposable container of claim 1, the improvement further comprising the provision of said indicia by molding said indicia into a surface of said open-topped box.

5. The hinged disposable container of claim 1, the improvement further comprising a plurality of said strips located in spaced, side-by-side relationship on the inside surface of at least one box, each of said strips defining a plurality of said slots, said indicia means being disposed immediately adjacent a slot whereby the indicia means assist the user in locating a slot for inserting an implement therein.

6. The hinged disposable container of claim 5, the improvement further comprising at least one strip on the inside surface of the other box.

* * * * *